United States Patent [19]

Ohmori et al.

[11] Patent Number: 4,587,165
[45] Date of Patent: May 6, 1986

[54] FILMS OF A COPOLYMER OF AN ESTER DERIVED FROM A FLUORINE-CONTAINING ALCOHOL

[75] Inventors: Akira Ohmori; Nobuyuki Tomihashi; Sinji Tamaru, all of Osaka, Japan

[73] Assignee: Daikin Kogyo Co., Ltd., Osaka, Japan

[21] Appl. No.: 639,855

[22] Filed: Aug. 13, 1984

Related U.S. Application Data

[63] Continuation of Ser. No. 440,305, Nov. 9, 1982, abandoned.

[30] Foreign Application Priority Data

Nov. 12, 1981 [JP] Japan ................. 56-182518
Nov. 24, 1981 [JP] Japan ................. 56-188973

[51] Int. Cl.⁴ .................................. C08F 14/18
[52] U.S. Cl. ...................... 428/334; 428/421; 526/246
[58] Field of Search ............... 428/334, 421; 526/246

[56] References Cited

U.S. PATENT DOCUMENTS 3,544,537 12/1970 Brace ............................. 526/246
4,170,687 10/1979 Spicer et al. .................... 428/421

Primary Examiner—Harry Wong, Jr.
Attorney, Agent, or Firm—Birch, Stewart, Kolasch & Birch

[57] ABSTRACT

An original plate for dry offset printing comprising a substrate suitable for preparation of an offset printing plate and a film formed on the substrate. The film consists essentially of a copolymer formed from at least 40% of a monomer of the formula:

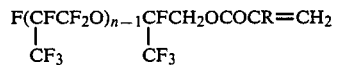

wherein n is an integer of 2 to 7 and R is hydrogen or methyl; and at least one other ethylenically unsaturated monomer.

15 Claims, No Drawings

FILMS OF A COPOLYMER OF AN ESTER DERIVED FROM A FLUORINE-CONTAINING ALCOHOL

This application is a continuation of copending application Ser. No. 440,305, filed on Nov. 9, 1982, now abandoned.

The present invention relates to a fluorine-containing alcohol and its derivatives, a polymer comprising acrylate or methacrylate of said alcohol and an ink repellent agent containing said polymer.

The fluorine-containing alcohol of the invention is representable by the formula:

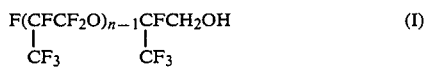

$$F(CFCF_2O)_{n-1}CFCH_2OH \qquad (I)$$
$$\quad\;\; | \qquad\qquad\; |$$
$$\quad CF_3 \qquad\quad CF_3$$

wherein n is an integer of 2 to 7. Its derivatives may be esters with organic or inorganic acids, alcoholates with alkali metals or alkaline earth metals, etc.

The compound (I) may be prepared by reducing a compound of the formula:

$$F(CFCF_2O)_{n-1}CFCOOCH_3 \qquad (III)$$
$$\quad\;\; | \qquad\qquad\; |$$
$$\quad CF_3 \qquad\quad CF_3$$

wherein n is as defined above. As a reducing agent, lithium aluminum hydride, sodium borohydride, lithium borohydride, a combination of hydrogen and platinum oxide or palladium, a combination of sodium and alcohol, etc. are preferably used. The reduction may be carried out in a solvent at a temperature of from 5° to 100° C., preferably a reflux temperature of the solvent. Examples of the solvent are diethylether, dibutylether tetrahydrofuran, dioxane, N-methylmorpholine, methanol, etc. The reaction pressure may be atmospheric pressure when the solid reducing agent is used, and from atmospheric pressure to 150 atm when hydrogen is used as the reducing agent. The amount of the reducing agent is usually from a stoichiometric amount to 10 times the stoichiometric amount. For example, a half mole of lithium aluminum hydride is used to 1 mole of the ester (III).

Acrylate and methacrylate (II) of the formula:

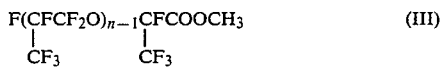

$$F(CFCF_2O)_{n-1}CFCH_2OCOCR=CH_2$$
$$\quad\;\; | \qquad\qquad\; |$$
$$\quad CF_3 \qquad\quad CF_3$$

wherein n is an integer of 2 to 7 and R is hydrogen or methyl, of the compound (I) are easily prepared, for instance, by reacting the compound (I) with acrylic acid and methacrylic acid respectively. The esterification is carried out usually at a temperature of from 40° to 130° C., preferably from 60° to 80° C. in the presence of a conventional esterification catalyst such as p-toluenesulfonic acid, sulfuric acid, boron trifluoride, hydrogen chloride or phosphoric acid, when desired, in an inert solvent such as benzene, toluene, xylene or ethylene dichloride. Favored is the presence of a polymerization inhibitor such as hydroquinone, methoxyhydroquinone, butylcatechol, ferric chloride and cupric chloride in the reaction system, the amount of which is from 0.5 to 3% by weight based on the total amount of the reactants. In order to complete the esterification, the by-produced water may be removed with a dehydrating agent such as phosphorous pentoxide or azeotropically by the aid of a suitable solvent such as benzene, toluene or xylene.

Alternatively, acrylate and methacrylate (II) of the compound (I) can be prepared by reacting the compound (I) directly with acryloyl chloride and methacryloyl chloride, respectively. The reaction is preferably carried out at a temperature of from 5° to 60° C. in the presence of the same polymerization inhibitor as used in the above reaction. As an acid acceptor, there may be used a basic substance such as triethylamine, pyridine or caustic alkali.

In either esterification reaction, the reaction pressure is usually atmospheric pressure. The molar ratio of the acid or the acyl chloride to the compound (I) is preferably from 1:1 to 2:1.

The amount of the catalyst, when used, is usually from 1 to 5% by weight based on the total weight of the reactants. The dehydrating agent may be employed in a stoichiometric amount or a slightly excess amount. The amount of the solvent is usually equal to that of the compound (I).

The alcoholate of the compound (I) is prepared by a conventional method, for example, by adding alkali or alkaline earth metal to the compound (I) or by adding an aqueous solution of alkali or alkali metal hydroxide to the compound (I) and heating the mixture at a temperature of from 60° to 120° C.

Acrylate or methacrylate (II) of the compound (I) can be homopolymerized or copolymerized with other monomers, preferably ethylenically unsaturated monomers.

Specific examples of the ethylenically unsaturated monomers are ethylene, halogenated vinyl, halogenated vinylidene, styrene, acrylic acid, methacrylic acid, alkyl acrylate or methacrylate, fluoroalkyl acrylate or methacrylate, benzyl acrylate or methacrylate, cyclohexyl acrylate or methacrylate, vinyl alkyl ketones, vinyl alkyl ether, butadiene, isoprene, chloroprene, maleic anhydride, etc.

For the use of the copolymer as an active component in an ink repellent agent, the content of acrylate or methacrylate (II) of the compound (I) is to be at least 40% by weight, preferably at least 70% by weight.

For polymerization, various modes such as bulk polymerization, solution polymerization, emulsion polymerization, radiation polymerization and plasma polymerization may be adopted. When the polymer is used as the active component of the ink repellent agent, it is preferably prepared by solution polymerization.

The polymerization is generally initiated by an organic or inorganic radical-producing agent. Examples of the radical-producing agent as an initiator are benzoyl peroxide, lauryl peroxide, acetyl peroxide, succinyl peroxide, sodium persulfate, hydrogen peroxide, azobisisobutylonitrile, 2,2'-azodiisobutylamidine dihydro chloride, cumen hydroperoxide, etc. The amount of the initiator is from 0.01 to 5% by weight on the basis of the weight of the monomer(s).

The polymerization is carried out at a temperature of from 20° to 100° C., preferably form 45° to 70° C.

In the solution polymerization, any good solvent for the resulting polymer is used. Examples of the good solvent are hexafluoro-m-xylene, trichlorotrifluoroethane, tetrachlorohexafluorobutane, etc. As the initiator, any conventional peroxides and aliphtic azo compounds may be used. Azobisisobutylonitrile and benzoil peroxide are most preferred.

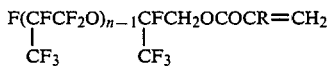

In the emulsion polymerization, the monomer(s) is emulsified in water in the presence of a surfactant and polymerized. As the initiator, peroxides, aliphatic azo compounds, persulfates and redox catalysts are preferably used. The surfactant as an emulsifier may be a conventional anionic, nonionic or cationic one or mixture of the nonionic one and at least one of the anionic or cationic ones. Specific examples of the emulsifier are sodium laurylsulfate, potassium perfluorosulfonate, trimethyltetradecylammonium chloride, sodium laurylsulfosuccinate and a condensate of ethylenoxide with alkylphenol or alkylamine.

The polymer of the invention has excellent water- and oil-repellency, particularly ink repellency, and is advantageously used as an ink repellent film in dry offset printing, namely offset printing that requires no dampening water.

The ink repellent film may be prepared from a solution or a dispersion of the polymer. For the production of an original plate for the dry offset printing, the solution or the dispersion containing, for example, 3 to 15% by weight of the polymer is coated on a substrate such as a metal plate (e.g. an aluminum plate, a zinc plate, an iron plate, etc.), paper and plastics having good dimensional stability (e.g. polyethylene film) by means of a bar coater or a spin coater, evaporating the solvent or water and, if necessary, heating the plate to form a film of the polymer having thickness of usually from 0.5 to 20 μm.

For the production of a lithographic plate from the original plate, the original plate is broken down partly by laser radiation or electric discharge, and the broken down part is converted to an ink-accepting part. Alternatively, a toner image is transferred to the original plate by means of electrophotographic method and heat fixed and used as an ink-accepting part.

The present invention will be hereinafter explained further in detail by the following Examples.

EXAMPLES 1(1)–1(3)

To a one liter four-necked flask equipped with a stirrer, a thermometer, a reflux condenser and a dropping funnel, lithium aluminum hydride (5.5 g) was charged and the flask interior was replaced with nitrogen gas. After diethyl ether (200 ml) was added through the dropping funnel, a solution of

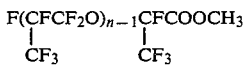

(0.1 mole, 34.4 g when n=1, 51.0 g when n=3 or 67.6 g when n=4) in diethyl ether (200 ml) was dropwise added over about 2 hours. The mixture was then heated to reflux for 15 minutes. Water was added to decompose excess lithium aluminum hydride, and dilute hydrochloric acid was added to acidify the mixture. The organic layer was separated and distilled to obtain

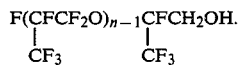

The boiling point and the yield of the obtained compound are shown in Table 1.

TABLE 1

| Example | n | Boiling point | Yield (%) |
| --- | --- | --- | --- |
| 1(1) | 2 | 118° C./760 mmHg | 84 |
| 1(2) | 3 | 156° C./760 mmHg | 85 |
| 1(3) | 4 | 100° C./30 mmHg | 82 |

EXAMPLES 2(1)–2(4)

To a 300 ml flask equipped with a stirrer, a thermometer and a reflux condenser, benzene (50 g), methacrylic acid (24 g, 0.28 mole),

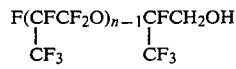

(0.1 mole, 31.6 g when n=2, 48.2 g when n=3, 64.8 g when n=4 or 81.4 g when n=5) and hydroquinone (0.1 g) were charged and heated to 80° C. At the same temperature, phosphorus pentachloride (25 g) was added by portions. After the reaction was completed, the reaction mixture was cooled. Then, the organic layer was separated, washed with a dilute aqueous solution of sodium sulfate and distilled under reduced pressure to obtain

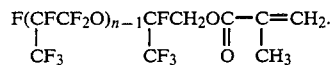

The boiling point, the yield and the refractive index $n_D^{25}$ of the obtained compound are shown in Table 2.

TABLE 2

| Example | n | Boiling point | Yield (%) | $n_D^{25}$ |
| --- | --- | --- | --- | --- |
| 2(1) | 2 | 50° C./20 mmHg | 82 | 1.321 |
| 2(2) | 3 | 65° C./5 mmHg | 75 | 1.315 |
| 2(3) | 4 | 99° C./7 mmHg | 78 | 1.314 |
| 2(4) | 5 | 116° C./5 mmHg | 72 | 1.309 |

EXAMPLES 3(1)–3(3)

The polymers of the fluorine-containing methacrylates obtained in Examples 2(2)–2(4) were prepared.

The fluorine-containing methacrylate (10 g), hexafluoro-m-xylene (20 g) and azobisisobutylonitrile (0.1 g) were charged in a glass ampule, cooled in a dry ice-methanol bath, degassed and sealed. The sealed ampule was kept in a constant temperature bath kept at 60° C. for 24 hours. Then, the reaction mixture was added to petroleum ether by portions with stirring. The precipitate was filtered and dried at 130° C. under a pressure of 10 mmHg for 20 hours to obtain the polymer as a transparent rubbery mass.

The yield, the refractive index $n_D^{25}$ and the glass transition temperature Tg of the obtained polymer are shown in Table 3.

TABLE 3

| Example | n | $n_D^{25}$ | Tg (°C.) | Yield (%) |
| --- | --- | --- | --- | --- |
| 3(1) | 3 | 1.3410 | −9 | 83 |
| 3(2) | 4 | 1.3320 | −40 | 72 |
| 3(3) | 5 | 1.3265 | −40 | 68 |

EXAMPLES 4(1)–4(7)

The copolymers of

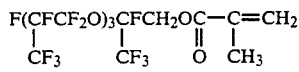

with various ethylenically usaturated monomers were prepared by bulk polymerization.

The predetermined amounts of the fluorine-containing methacrylate and of the ethylenically unsaturated monomer and azobisisobutylonitrile (0.1 g) were charged and polymerized in the same manner as in Example 3. The polymer was obtained as a transparent mass. The refractive index $n_D^{25}$ of the obtained polymer is shown in Table 4.

TABLE 4

| Example | Ethylenically unsaturated monomer | Amount of methacrylate (g) | $n_D^{25}$ of polymer |
|---|---|---|---|
| 4(1) | $C_8F_{17}CH_2CH_2OC(=O)C(CH_3)=CH_2$ (1) | 9 | 1.344 |
| 4(2) | $C_8F_{17}CH_2CH_2OC(=O)C(CH_3)=CH_2$ (2) | 5 | 1.355 |
| 4(3) | $C_9F_{19}CH_2CH_2OC(=O)C(CH_3)=CH_2$ (1) | 9 | 1.342 |
| 4(4) | Methyl methacrylate | (1) 9 | 1.358 |
| 4(5) | Methacrylic acid | (1) 9 | 1.362 |
| 4(6) | Styrene | (1) 9 | 1.373 |
| 4(7) | Methyl acrylate | (1) 9 | 1.354 |

REFERENCE EXAMPLES 1 AND 2

In the same manner as in Example 3 but using $C_8F_{17}CH_2CH_2OCOC(CH_3)=CH_2$ (Reference Example 1) or $C_9F_{19}CH_2CH_2OCOC(CH_3)=CH_2$ (Reference Example 2), the polymerization was carried out to obtain the polymer as a transparent mass.

EXAMPLES 5(1)–5(11) AND COMPARATIVE EXAMPLES 1 AND 2

The polymers shown in Table 5 were tested for ink-repellent properties.

The polymer was dissolved in hexafluoro-m-xylene to prepare a solution of a concentration of 10% by weight.

The thus prepared solution was applied on a clean surface of an aluminum plate of 0.3 mm thick by means of a bar coater, dried and heated at 130° C. for 10 minutes to obtain an aluminum test plate coated with polymer film of 10 to 20 microns thick.

The test plate was set on a master cylinder of an offset printing machine (Toko Type-810, Tokyo Kokukeiki Kabushikikaisha). The printing machine was operated with the supply of ink but no water and paper. After 500 or 2,000 revolutions of the master cylinder, the machine was stopped, and the ink adhered on the test plate was transferred to a white paper.

The relative reflectance of the inked paper was measured by a reflectometer (RM-50, Kabushikikaisha Murakami Skikisai Kenkyusho), reflectance of the white paper being 100%. A higher value of the relative reflectance shows better ink repellency.

The ink used is offset printing ink (SP highness black, manufactured by Osaka Ink Kabushikikaisha) and dry offset printing ink (WLP-black S, manufactured by Osaka Ink Kabushikikaisha).

The results are shown in Table 5.

TABLE 5

| | | Relative reflectance (%) | | | |
| | | Offset printing ink | | Dry offset printing ink | |
| Polymer | | 500 revs. | 2,000 revs. | 500 revs. | 2,000 revs. |
|---|---|---|---|---|---|
| Example 5(1) | Homopolymer of methacrylate (II) (n = 2) | 15 | 10 | 94 | 96 |
| Example 5(2) | Homopolymer of methacrylate (II) (n = 3) | 12 | 14 | 93 | 92 |
| Example 5(3) | Homopolymer of methacrylate (II) (n = 4) | 16 | 17 | 94 | 98 |
| Example 5(4) | Homopolymer of methacrylate (II) (n = 5) | 20 | 19 | 96 | 99 |
| Example 5(5) | Copolymer in Example 4(1) | 18 | 17 | 92 | 94 |
| Example 5(6) | Copolymer in Example 4(2) | 16 | 15 | 98 | 91 |
| Example 5(7) | Copolymer in Example 4(3) | 13 | 12 | 91 | 92 |
| Example 5(8) | Copolymer in Example 4(4) | 8 | 12 | 93 | 95 |
| Example 5(9) | Copolymer in Example 4(5) | 7 | 10 | 89 | 87 |
| Example 5(10) | Copolymer in Example 4(6) | 11 | 13 | 88 | 89 |
| Example 5(11) | Copolymer in Example 4(7) | 14 | 17 | 98 | 94 |
| Comparative Example 1 | Polymer in Ref. Example 1 | 3 | 1 | 78 | 76 |
| Comparative Example 2 | Polymer in Ref. Example 2 | 6 | 5 | 81 | 83 |

What is claimed is:

1. An original plate for dry offset printing comprising a substrate suitable for preparation of an offset printing plate and a film formed on said substrate, said film consisting essentially of:

a copolymer formed from at least 40% by weight of a monomer of the formula:

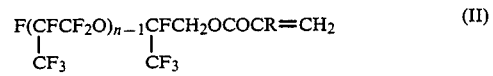

wherein n is an integer of 2 to 7 and R is hydrogen or methyl; and at least one other ethylenically unsaturated monomer.

2. The plate of claim 1, wherein said other monomer is selected from the group consisting of ethylene, styrene, acrylic acid, methacrylic acid, alkyl acrylate, alkyl methacrylate, fluoroalkyl acrylate, fluoroalkyl methacrylate, benzyl acrylate, benzyl methacrylate, cyclohexyl acrylate, cyclohexyl methacrylate, vinyl alkyl ketones, vinyl alkyl ether, butadiene, isoprene, chloroprene and maleic anhydride.

3. The plate of claim 1, wherein the film has a thickness of 0.5 to 20 μm.

4. An original plate for dry plate offset printing comprising a substrate suitable for preparation of an offset printing plate and a film having a thickness of from 0.5 to 20 μm formed on said substrate, said film consisting essentially of a copolymer formed from at least 40% by weight of a monomer of the formula:

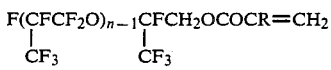 (II)

wherein n is an integer of 2 to 7 and R is hydrogen or methyl and at least one other ethylenically unsaturated monomer selected from the group consisting of ethylene, styrene, acrylic acid, methacrylic acid, alkyl acrylate, alkyl methacrylate, fluoroalkyl acrylate, fluoroalkyl methacrylate, benzyl acrylate, benzyl methacrylate, cyclohexyl acrylate, cyclohexyl methacrylate, vinyl alkyl ketones, vinyl alkyl ether, butadiene, isoprene, chloroprene and maleic anhydride.

5. The plate of claim 4, wherein the monomer (II) is present in an amount of at least 70% by weight.

6. The plate of claim 4, wherein said monomer of the formula (II) is:

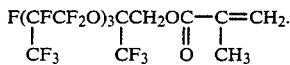

7. The plate of claim 4, wherein said ethylenically unsaturated monomer is:

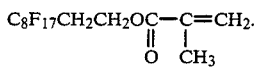

8. The plate of claim 4, wherein said ethylenically unsaturated monomer is:

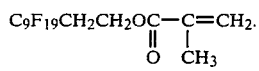

9. The plate of claim 4, wherein said ethylenically unsaturated monomer is methyl methacrylate.

10. The plate of claim 4, wherein said ethylenically unsaturated monomer is methacrylic acid.

11. The plate of claim 4, wherein said ethylenically unsaturated monomer is styrene.

12. The plate of claim 4, wherein said ethylenically unsaturated monomer is methyl acrylate.

13. The plate of claim 4, wherein said ethylenically unsaturated monomer is fluoroalkyl acrylate or fluoroalkyl methacrylate.

14. An original plate for dry offset printing comprising a substrate suitable for preparation of an offset printing plate and a film formed on said substrate, said film consisting essentially of:

a homopolymer formed from a monomer of the formula:

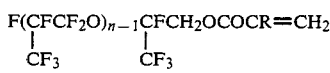 (II)

wherein n is an integer of 2 to 7 and R is hydrogen or methyl.

15. The plate of claim 14, wherein the film has a thickness of 0.5 to 20 μm.

* * * * *